United States Patent [19]

Aagard

[11] Patent Number: 4,487,206

[45] Date of Patent: Dec. 11, 1984

[54] FIBER OPTIC PRESSURE SENSOR WITH TEMPERATURE COMPENSATION AND REFERENCE

[75] Inventor: Roger L. Aagard, Richfield, Minn.

[73] Assignee: Honeywell Inc., Minneapolis, Minn.

[21] Appl. No.: 434,028

[22] Filed: Oct. 13, 1982

[51] Int. Cl.³ .............................................. A61B 5/02
[52] U.S. Cl. .................................... 128/667; 128/634; 128/673; 73/705
[58] Field of Search ................................ 128/672–673, 128/675, 748, 667, 634; 73/705, 708, 715

[56] References Cited

U.S. PATENT DOCUMENTS

| | | | |
|---|---|---|---|
| 3,215,135 | 11/1965 | Franke | 128/675 |
| 3,249,105 | 5/1966 | Polanyl | 128/675 |
| 3,267,932 | 8/1966 | Valliere | 128/675 |
| 3,273,447 | 9/1966 | Frank | 128/675 X |
| 3,580,082 | 5/1971 | Strack | 73/715 X |
| 3,686,958 | 8/1972 | Porter et al. | 128/748 X |
| 3,789,667 | 2/1974 | Porter et al. | 128/748 X |
| 4,127,114 | 11/1978 | Bretscher | 128/667 |
| 4,158,310 | 6/1979 | Ho | 73/705 |
| 4,210,029 | 7/1980 | Porter | 128/748 X |

FOREIGN PATENT DOCUMENTS 655384  4/1979  U.S.S.R. .............................. 128/748

OTHER PUBLICATIONS

Lekholm et al., "Optoelectronic Transducer for Intravascular Measurements of Press. Variations", *Med. and Biol. Engng.*, vol. 7, 1969, pp. 333–335.

Primary Examiner—Lee S. Cohen
Assistant Examiner—Angela D. Sykes
Attorney, Agent, or Firm—Omund R. Dahle

[57] ABSTRACT

An intravascular catheter tip fiber optic pressure sensor wherein a lens element at the end of the fiber optic collimates the light emanating from the fiber and directs the light in a column towards a closely spaced reflecting diaphragm. The diaphragm is pressure responsive and modulates the focal length of the lens-diaphragm-mirror combination. Three optic fibers traverse the length of the hollow catheter tube, one carrying transmitted light to the tip, one carrying the reflected light from the diaphragm (i.e. the signal), and the third fiber carrying a reflected reference light. The reference detector provides a signal level to control the level of intensity of the light source.

11 Claims, 4 Drawing Figures

FIBER OPTIC PRESSURE SENSOR WITH TEMPERATURE COMPENSATION AND REFERENCE

BACKGROUND AND SUMMARY OF THE INVENTION

The present invention relates to the measurement of pressure. Specifically, the disclosed embodiments describe an intravascular catheter tip pressure sensor but the present invention is not to be limited to the measuring of intravascular blood pressure.

Measurements of intravascular blood pressure are usually performed with a hollow catheter tube filled with saline solution and attached to an external transducer. This has the drawback of poor frequency response due to the long fluid column. In addition, saline solution is a poor dielectric, making electrical shock hazards a concern.

Catheter tip sensors have been proposed in which light from one or more fibers in a bundle is reflected off a mirrored diaphragm and back into different optical fibers. Pressure induced motion of the diaphragm modulates the intensity of the returned light which is then measured to infer pressure. One such pressure transducer is disclosed in the Strack U.S. Pat. No. 3,503,116 and its division U.S. Pat. No. 3,580,082.

In my earlier copending patent application Ser. No. 298,972, entitled "Fiber Optic Pressure Sensor", filed Sept. 3, 1981, now abandoned and assigned to the same assignee as the present invention, a fiber optic pressure sensor is described in which a reflecting diaphragm modulates the focal length of a lens-mirror combination. A pressure deformable single reflecting curved diaphragm is used as an optical element together with a lens or refracting element on the optical fiber end. The lens element collimates the cone of light emanating from the fiber and directs the light in a column towards the reflecting diaphragm, the diaphragm being separated by a very small distance from the lens. This refracting element on the end of the optic fiber preferably is a molded optical plastic lens such as a lucite member with a spherically curved surface.

In the present invention which is an improvement of my earlier copending application, above referred to, there is provided compensation for temperature as well as a reference sensor in addition to the earlier apparatus.

DESCRIPTION

Figure 1:
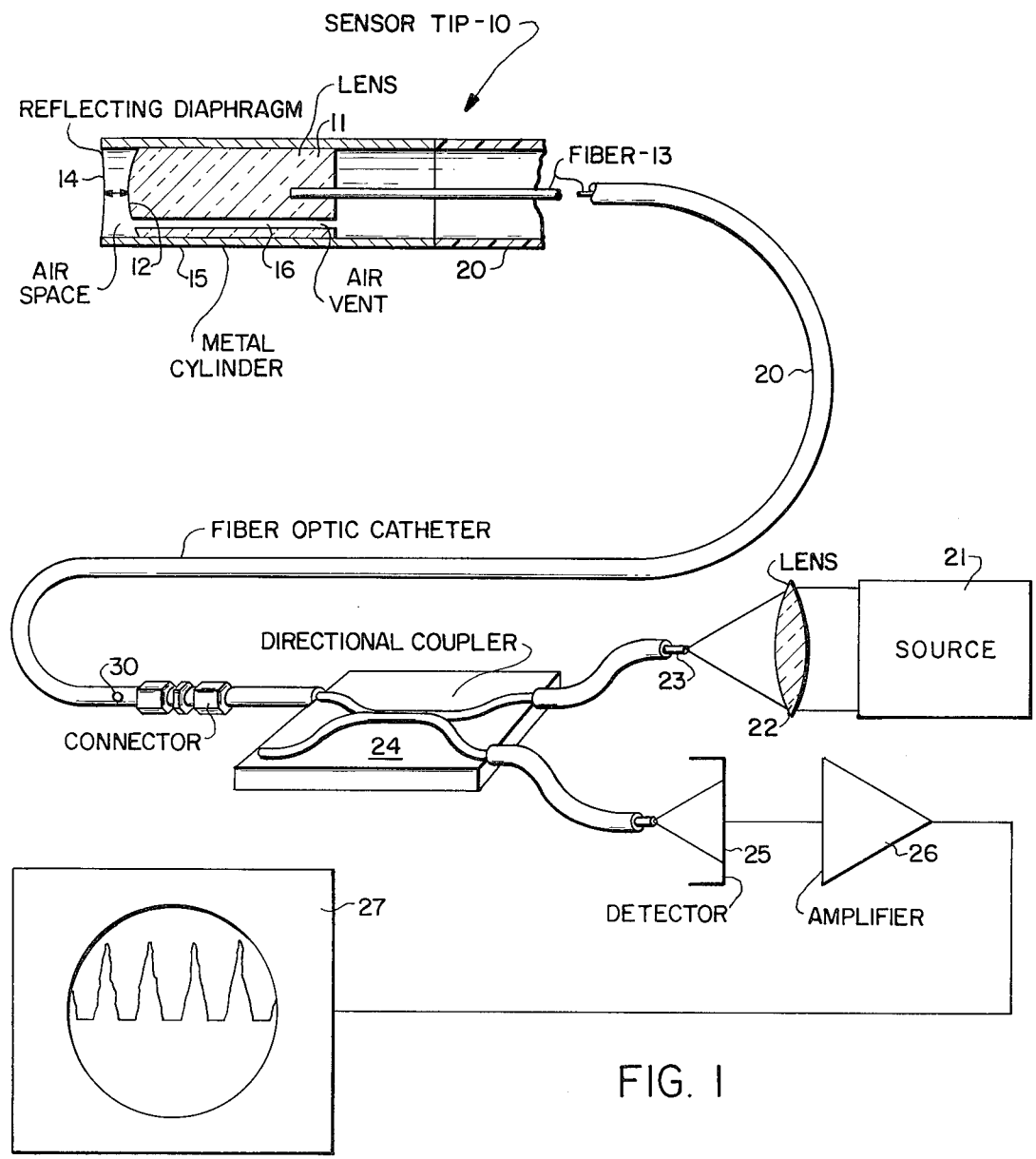
FIG. 1 is a prior art schematic diagram of an embodiment of my earlier application.

In my earlier invention shown in FIG. 1 there is pictured in somewhat schematic form a single fiber embodiment of the fiber optic pressure sensor apparatus commencing with a catheter sensing tip 10. The sensing tip 10 comprises a molded optical plastic lens 11 having a spherically curved surface 12 at the face opposite that into which the optic fiber 13 is fastened. The tip also comprises a thin polyester reflecting diaphragm 14 which is spaced and fastened a small distance away from the lens by a cylinder member 15. The diaphragm may also be stainless steel, aluminum, brass or other suitable material. The diaphragm is pressure responsive. An air vent 16 in the form of a small hole through the lens allows the pressure inside the tip between the diaphragm and lens to equalize with the atmospheric pressure. The lens 11 is specifically designed to collimate or nearly collimate the cone of light emanating from the fiber 13 and to direct the light to the reflecting diaphragm 14. Although the lens is described as a conventional molded optical plastic lens, the lens may be of other light collimating types such as a graded index lens, often called GRIN or Selfoc, for example. The pressure deformable mirror diaphragm cooperates with the lens as a lens-mirror-lens optical system, with the diaphragm modulating the effective focal length of the lens-mirror combination. The diaphragm is shown in a deformed position resulting from pressure against the outside; with no pressure the diaphragm will be more flat.

The sensing tip portion 10 of the pressure catheter is shown much enlarged in FIG. 1 for purposes of clarity in explanation. The sensing tip is affixed at the end of a hollow catheter tube 20. The sensor tip is of the same diameter as the catheter and the optical fiber 13 is small in diameter and fits inside the hollow catheter. The catheter 20 near the connector has an aperture 30 for communicating atmospheric pressure to the inside of diaphragm 14. A light source 21 and suitable lens 22 focuses the light into the other end 23 of the fiber optic. The light source 21 may also be a solid state light source which abuts directly against the end of the fiber. A conventional directional coupler 24 transmits the light from the source to the fiber 13 and channels the reflected light to a detector 25. The electrical signal processing electronics such as an amplifier 26 and display 27 receive the signals from the detector 25 for converting the optical signal to an electrical signal which can be further conditioned, displayed or recorded. In the undistorted position of the mirror diaphragm the fiber end is imaged onto itself with unit magnification. When the mirror diaphragm is distorted by pressure, the radiation is spread to cover a larger area, that is, the focal length of the lens-mirror combination is changed. Thus the amount of reflected light collected by the fiber varies as a function of the pressure.

Figure 2:
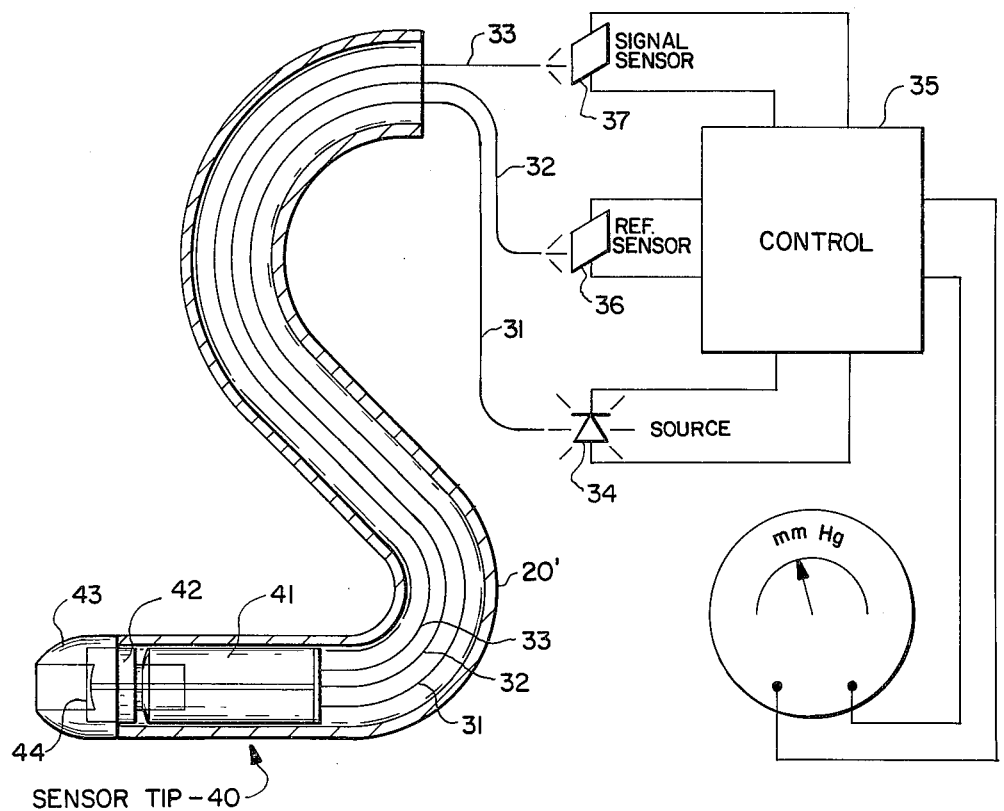
FIG. 2 is a schematic diagram of the present invention.
Figure 3:
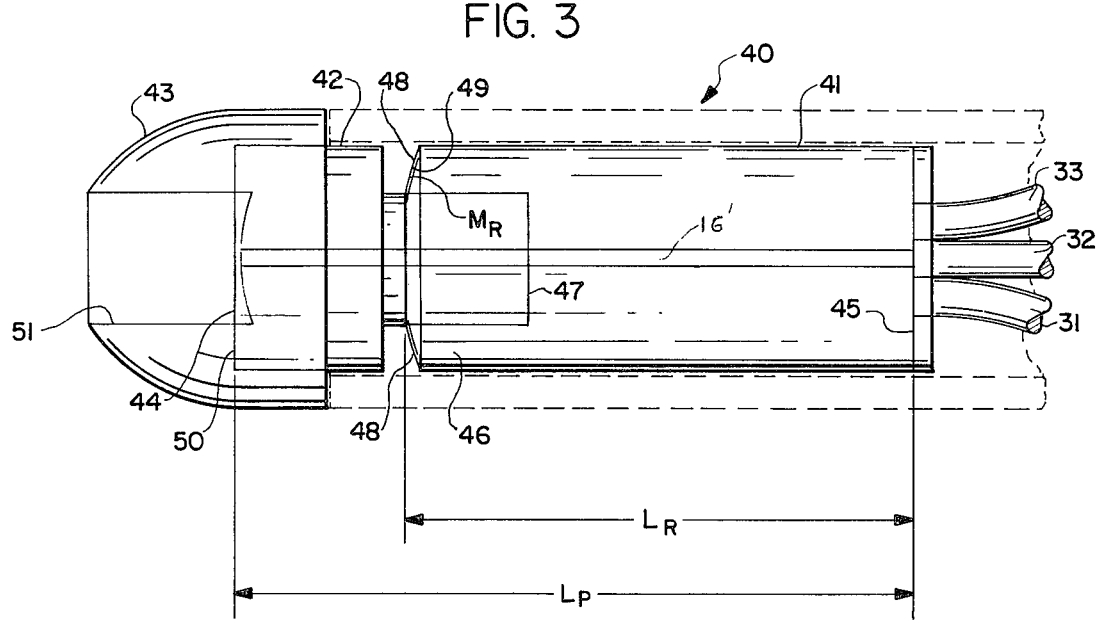
FIG. 3 is an enlargement of a portion of FIG. 2.

Referring now to my improved fiber optic pressure sensor apparatus shown in FIGS. 2 and 3, there is shown a hollow catheter tube 20' having encased therein three optic fibers 31, 32 and 33. A light source 34, such as an LED, which receives power from a control means 35, directs light into the fiber 31 which carries the light to the sensor tip assembly 40 affixed at the end of the catheter tube 20'. Reflected light returning from the tip through optic fibers 32 and 33 is sensed by reference sensor detector 36 and signal sensor detector 37, respectively, and the electrical signals from these detectors are connected to the control means 35. The ends of the fibers 31, 32 and 33 are bonded to a plastic body in the sensor tip assembly 40. As shown, the tip assembly consists of four parts: body 41, lens 42, tip 43 and diaphragm 44. The body, lens and tip may all be constructed of a transparent (to visible light) plastic such as lucite. The body and lens must be transparent; the tip need not be. The body 41 and lens 42 have a small bore or groove therethrough (similar to FIG. 1) to allow air to pass through them from the hollow catheter tube 20' to the diaphragm. The diaphragm 44 may be formed from the materials suggested above for diaphragm 14. The body 41 is machined or molded at a first end 45 to accommodate the three optical fibers (signal 33, reference 32 and source 31). The fibers are bonded in place with an (approximately) index-matching adhesive. At a second end 46 the body is recessed at 47 and accommodates the lens 42, which is also secured with an (approximately) index-matching adhesive. The periphery 48 of the second end is preferably spherical so that when it is coated with a reflective metal such as aluminum it forms a ring-like spherical, annular mirror 49 surrounding the lens for reflecting light within the body of the tip assembly. The coating operation may preferably be done before inserting the lens, and may be accomplished using standard vapor-phase deposition methods. Finally, the tip 43 clamps the diaphragm 44 against the ring 50 that surrounds the refractive element. The tip has a bore 51 filled with silicone rubber for transmission of the intravascular blood pressure to the diaphragm 44 and forming an airtight seal and has a rounded leading edge to minimize tissue damage and to allow for easy insertion.

The operation of the improved sensor will now be described. The light produced by the LED 34 is carried to the tip assembly 40 by the source fiber 31. Upon exiting the source fiber, the light emanates into the body 41 in a cone-like shape. Some of the light enters the lens 42 but a portion of the light strikes the spherical annular mirrored surface 49 at the lens end of the body 41. The radius of the mirror 49 is such that the incident light is reflected in a focused fashion onto the tip of the reference fiber 32. The light that enters the lens 42 is collimated or nearly collimated thereby and the collimated light is directed to the diaphragm 44, where it is reflected and subsequently refracted onto the tip of signal fiber 33. Thus the source light is divided, some of the source light never strikes the lens and diaphragm but is simply reflected by mirror 49 into the reference fiber 32, and some of the source light reaching the diaphragm is reflected into the signal fiber 33, the amount depending on the curvature of the diaphragm 44.

It can readily be seen that the amount of light reflected to and carried by the reference fiber 32 depends on the intensity of source 34. For example, if the source intensity decreases due to a drop in electrical power supplied to the LED, the amount of light reflected into the reference fiber 32 also decreases. The amount of light that reaches the tip assembly is also affected by the extent and number of bends in the source fiber (bending causes optical coupling of the core and the fiber cladding). Therefore, the amount of light reflected from mirror 49 and into the reference fiber is a function of bending of the fiber. Note that the light reflected into the reference fiber is unaffected by the pressure differential across the diaphragm.

Figure 4:
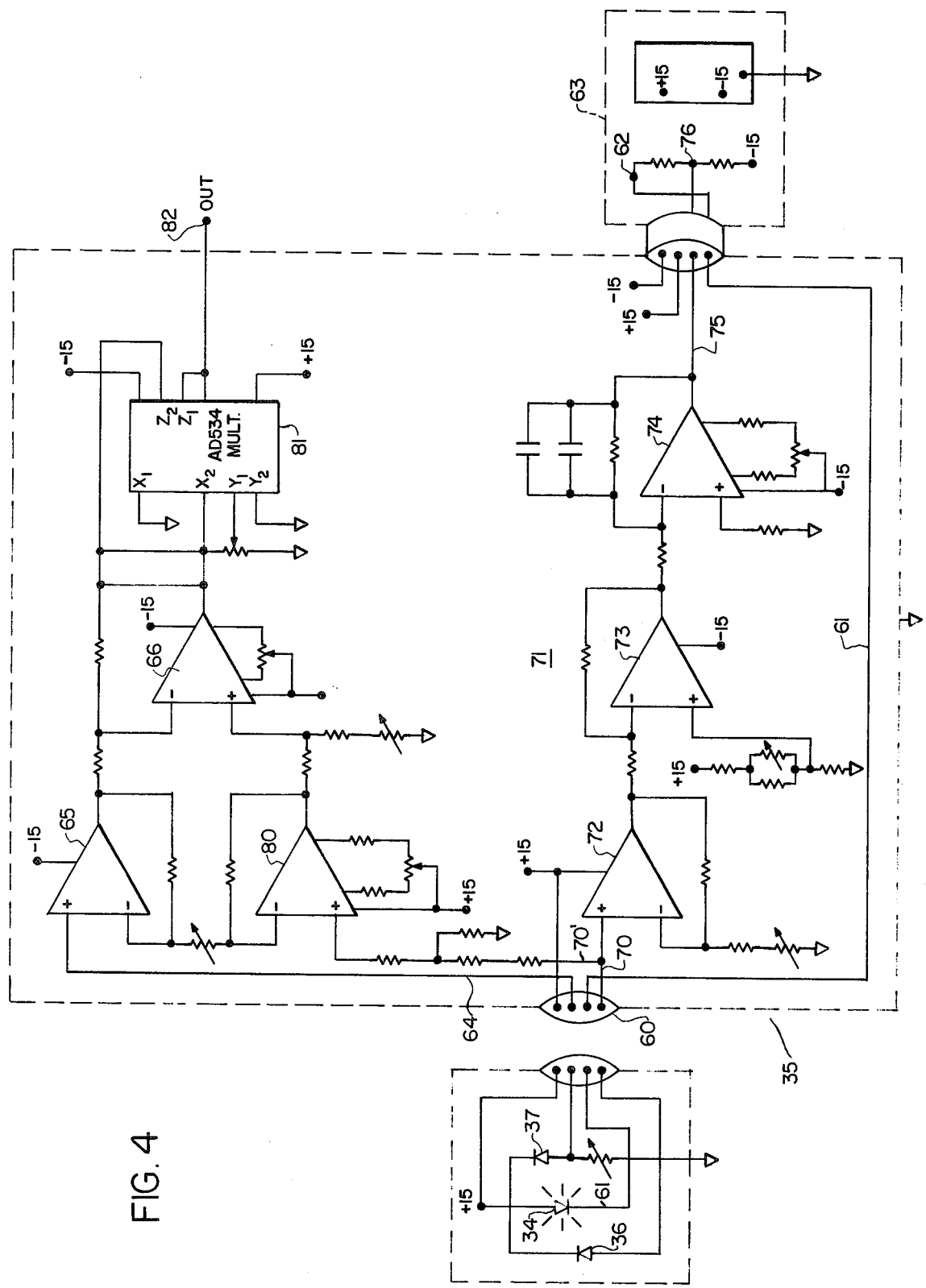
FIG. 4 is an electrical circuit diagram of the present invention.

In FIG. 4 there is shown a typical circuit schematic of the control means 35. The control means contains circuitry which compensates for source intensity fluctuations and fiber bending. At the left of the figure are shown the light source 34, the reference sensor 36 and the signal sensor 37 making connections to the control means 35 at connector 60. The LED 34 is connected by a conductor 61 to a controllable output 62 of a power module 63, which power module also provides a +15 volts and a −15 volts DC. The signal output from signal sensor 37 is connected by a conductor 64 to the positive input of an op amp 65, the output of which is connected to the negative input of op amp 66. The signal output from reference sensor 36 is connected by a conductor 70 to a low frequency amplifier 71 comprising op amp 72, op amp 73 and op amp 74. The output of op amp 74 is connected by a conductor 75 to the power supply module at point 76 to adjust the output voltage at terminal 62 in response to signal level at the reference sensor 36. The signal output of the reference sensor 36 is also connected to conductor 70' and a resistive network to the positive input of op amp 80, the output of which is connected to the positive input of op amp 66. The op amp 66 then provides a common mode rejection for high frequency noise such as may arise from the light source. The output signal of op amp 66 is connected into a multiplier 81 which introduces a linearizing component to the signal before providing an output signal at terminal 82.

In operation of the improved system the electrical power supplied to the source 34 is controlled and responds to "slow" changes in the light received by the reference sensor 36 in order to maintain the reference light at a constant level. "Slow" changes might be caused by fiber bending, changes in electrical power supplied to the source or temperature changes. Slow changes in the reference and signal might also be caused by changes in temperature at the tip assembly, but such changes are substantially eliminated by the proper choice of the dimensions $L_P$, $L_R$ and the radius of $M_R$. "Fast" changes in the reference signal, caused by, for example, quantum efficiency fluctuations in the source, are not compensated for by controlling the intensity of the source. They are "common mode rejected" by op amp 80 shown in FIG. 4. Thus, the circuit shown in FIG. 4 rejects "fast" common mode disturbances while simultaneously controlling the source in response to "slow" changes in the reference signal to maintain a constant source intensity. Fluctuations in the signal that do not appear on the reference are indicative of true fluctuations in the pressure differential across the diaphragm, and are therefore amplified and made available for a gage or other readout. Thus the improved sensor compensates for slow changes in the reference by controlling the source intensity.

The embodiments of the invention in which an exclusive property or right is claimed are defined as follows:

1. An intravascular blood pressure catheter of the fiber optic type comprising:
   a catheter member containing at least three optic fibers including a source fiber, a signal fiber and a reference fiber;
   a catheter sensing tip including a pressure deformable diaphragm with an inside face, the diaphragm having a reflecting surface finish on the inside face;
   means for directing a source of light through said source optic fiber toward said tip, said source of light being controlled in intensity;
   a transparent body fastened to an end of said fibers into which body light emanates from said source fiber, said body including light-collimating lens means for redirecting light emanating from the source fiber into a column toward said reflecting surface finish and for directing reflected light therefrom falling on said lens means towards said signal optic fiber, said body further including mirror means positioned to receive a portion of the light transmitted into said body from said source optic fiber and oriented to reflect said portion into said reference fiber;

signal sensing means for detecting the intensity of reflected light being returned in said signal optic fiber, the amount of light collected by the signal fiber being a function of the pressure;

reference sensing means for detecting the intensity of reflected light being returned in said reference fiber; and, control means responsive to the output of said reference sensing means to control the intensity of said source of light.

2. The apparatus according to claim 1 in which said control means is effective to adjust the current supplied to said source of light to thereby control its intensity.

3. The apparatus according to claim 1 in which said mirror means is a spherical annular mirrored surface on said transparent body.

4. The apparatus according to claim 3 in which said spherical annular mirrored surface has a radius such that the received light portion is reflected in a focused fashion onto the end of the reference fiber.

5. The apparatus according to claim 3 in which said spherical annular mirrored surface surrounds the lens means of said transparent body.

6. The apparatus according to claim 1 and further comprising:

circuit means receiving electrical outputs from both said signal sensing means and said reference sensing means and differentially combining the outputs to thereby provide a common mode rejection of high frequency noise components in the received signal output.

7. The apparatus according to claim 1 in which the mirror means is an annular ring-like reflector around the lens means.

8. The apparatus according to claim 1 in which there is a sealed air chamber between said diaphragm and said lens means and in which there is an air passage from said chamber to the catheter member so that ambient atmospheric pressure can be communicated to said chamber.

9. The apparatus according to claim 1 in which said lens means and said pressure deformable diaphragm forms a lens-mirror-lens combination of which said diaphragm modulates the focal length.

10. An intravascular blood pressure catheter of the fiber optic type comprising:

a catheter member comprising a hollow catheter tube containing a transmit optic fiber and two return optic fibers, one of said return fibers being a signal fiber and the other of said return fibers a reference fiber;

a catheter sensing tip including a pressure deformable diaphragm with an inside face, the diaphragm having a reflecting surface finish on the inside face;

means for directing a source of light through said transmit optic fiber to said tip;

light-collimating lens means at the tip of said transmit optic fiber for redirecting the light emanating from the fiber into a column to said diaphragm and for directing the light from said reflecting surface finish falling on said lens means towards said signal optic fiber;

sensing means for detecting the intensity of reflected light in said signal optic fiber, the intensity of said detected light being a function of pressure;

mirror means positioned to intercept a portion of the light emanating from said transmit fiber and to reflect said intercepted light to said reference optic fiber; and, sensing means for detecting the intensity of reflected light in said reference optic fiber.

11. The apparatus according to claim 10 in which said lens means and said pressure deformable diaphragm forms a lens-mirror-lens combination of which said diaphragm modulates the focal length.

* * * * *